(12) United States Patent
Mahieux et al.

(10) Patent No.: US 11,252,975 B2
(45) Date of Patent: Feb. 22, 2022

(54) CAFFEINE PRODUCTION METHOD (71) Applicant: SOCIETE DES PRODUITS NESTLE S.A., Vevey (CH)

(72) Inventors: Julien Philippe Nicolas Mahieux, Jougne (FR); Stefan Palzer, Lausanne (CH); Gerhard Niederreiter, Vevey (CH); Laurent Forny, Lausanne (CH); Federico Mora, Morges (CH); Bruno Edgar Chavez Montes, Lausanne (CH); Laure Poquet, Servion (CH); Heiko Oertling, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 141 days.

(21) Appl. No.: 16/650,022

(22) PCT Filed: Sep. 24, 2018

(86) PCT No.: PCT/EP2018/075754
§ 371 (c)(1),
(2) Date: Mar. 24, 2020

(87) PCT Pub. No.: WO2019/063465
PCT Pub. Date: Apr. 4, 2019

(65) Prior Publication Data
US 2020/0275675 A1    Sep. 3, 2020

(30) Foreign Application Priority Data
Sep. 29, 2017 (EP) ..................... 17193998

(51) Int. Cl.
*A23F 5/00*    (2006.01)
*B01D 9/00*    (2006.01)
*A23F 5/20*    (2006.01)
*B01D 11/02*   (2006.01)
*C07D 473/12*  (2006.01)

(52) U.S. Cl.
CPC .............. *A23F 5/206* (2013.01); *B01D 9/005* (2013.01); *B01D 11/0288* (2013.01); *C07D 473/12* (2013.01)

(58) Field of Classification Search
CPC ................................ A23F 5/206; B01D 9/005
See application file for complete search history.

(56) References Cited

U.S. PATENT DOCUMENTS 4,505,940 A    3/1985   Jones et al.
4,547,378 A    10/1985  Saleeb et al.

FOREIGN PATENT DOCUMENTS

EP    0340354    11/1989

OTHER PUBLICATIONS

Bucar et al. "Cocrystals of Caffeine and Hydroxybenzoic Acids Composed of Multiple Supramolecular Heterosynthons: Screening via Solution-Mediated Phase Transformation and Structural Characterization" Crystal Growth & Design, 2009, vol. 9, No. 4, pp. 1932-1943.

*Primary Examiner* — Sikarl A Witherspoon
(74) *Attorney, Agent, or Firm* — K&L Gates LLP (57) ABSTRACT

The present invention provides a method for producing caffeine, wherein the method comprises: (a) combining a coffee extract comprising caffeine with an aqueous organic acid; (b) crystallizing the coffee extract and the aqueous organic acid so as to form caffeine-organic acid co-crystals in an aqueous phase; (c) separating the caffeine-organic acid co-crystals from the aqueous phase; and (d) extracting caffeine from the co-crystals obtained in step (c), wherein step (d) comprises placing the co-crystals in an aqueous solution so as to form a caffeine precipitate and a solution comprising the organic acid. Also provided is a method for producing a decaffeinated coffee extract comprising chlorogenic acids.

17 Claims, 4 Drawing Sheets

CAFFEINE PRODUCTION METHOD

CROSS REFERENCE TO RELATED APPLICATIONS

The present application is a National Stage of International Application No. PCT/EP2018/075754, filed on Sep. 24, 2018, which claims priority to European Patent Application No. 17193998.6, filed on Sep. 29, 2017, the entire contents of which are being incorporated herein by reference.

FIELD OF THE INVENTION

The present invention generally relates to a method for producing caffeine. The method involves combining a coffee extract with an aqueous organic acid, forming caffeine-organic acid co-crystals and extracting the caffeine from the co-crystals using an aqueous solution. The present invention also provides a method for producing a decaffeinated coffee extract comprising chlorogenic acids.

BACKGROUND TO THE INVENTION

Decaffeination is a term used to describe the removal of caffeine from coffee beans, cocoa, tea leaves and other caffeine-containing materials. Decaffeinated products typically contain 1-2% of the original caffeine content, sometimes as much as 20%. For coffee, there are several decaffeination methods known in the art and in all these methods coffee is in its green, unroasted state.

One widely used method for decaffeinating coffee is the water decaffeination technique disclosed in U.S. Pat. No. 2,309,092. In this method hydrated green coffee beans are extracted with a caffeine-deficient green coffee extract in a multi-stage counter-current extraction battery. As the green coffee extract progresses through the battery, it becomes increasingly rich in caffeine while contacting decreasingly decaffeinated coffee beans. The caffeine-laden coffee extract withdrawn from the last stage of the battery is treated to remove caffeine therefrom and subsequently returned to the system. The caffeine is removed from the green coffee extract by contact with an organic solvent, typically a halogenated organic solvent such as methylene chloride.

However, whilst the water decaffeination method provides an extract containing a significant amount of caffeine, the use of an organic solvent to remove the caffeine from the green coffee extract means that it is not a food-grade process. The caffeine also includes impurities, and at least a portion of the chlorogenic acids present in the green coffee extract is lost on contact of the extract with the organic solvent.

Another known method for decaffeinating coffee is the $CO_2$ process, otherwise called the Liquid Carbon Dioxide method or the Supercritical Carbon Dioxide method. In this method water-soaked coffee beans are placed in an extraction vessel; the vessel is then sealed and supercritical $CO_2$ injected at a pressure of about 69 bar to selectively extract the caffeine. The caffeine-laden $CO_2$ is then transferred to another container where the pressure is released and the $CO_2$ returns to its gaseous state and evaporates, leaving the caffeine behind. The caffeine is removed using charcoal filters and the caffeine-free $CO_2$ is recycled back to the sealed extraction vessel. This process is food-grade because it avoids the use of potentially harmful substances. It is, however, very expensive to perform and does not provide an acceptable caffeine recovery yield. This process is therefore primarily used to decaffeinate large quantities of commercial-grade, less-exotic coffee.

U.S. Pat. No. 4,521,438 describes a method of decaffeinating aqueous coffee extracts. The method consists of adding caffeic acid to a caffeine-containing aqueous coffee extract to form an insoluble colloidal, caffeic acid/caffeine complex, growing crystals of the insoluble caffeic acid/caffeine complex, and separating the crystals from the decaffeinated liquid.

There remains a need in the art for a method for producing caffeine which:
(a) does not involve the use of potentially harmful substances such as organic solvents,
(b) produces caffeine in a substantially pure form; and/or
(c) is economically attractive.

Along with caffeine, coffee beans may be used to produce chlorogenic acids. Chlorogenic acids are naturally present in green, unroasted coffee beans and on hydrolysis form phenolic acids and quinic acid. The antioxidant activity of the phenolic acids produced from coffee is known to protect against "oxidative stress" by reducing damaging free radicals that may be implicated, e.g. in cancer, heart disease, degenerative brain disorders and ageing. Quinic acid is also believed to have health benefits, for example, due to its in-situ effect on antioxidants in the human body (Pero et al., International Journal of Biotechnology and Biochemistry (2009) 5, 293-305).

There is also therefore a desire in the art to produce a source of chlorogenic acids from a coffee extract.

SUMMARY OF THE INVENTION

The present inventors have surprisingly found a method for producing caffeine which does not use an organic solvent and which produces caffeine in a high yield and a substantially pure form. In particular the inventors have found that by using an aqueous solution to extract caffeine from caffeine-organic acid co-crystals formed from a coffee extract comprising caffeine, and an aqueous organic acid, the above-mentioned needs can be met. As the coffee extract used in the present invention may be a by-product or side-stream from a coffee decaffeination process, the method is also economically attractive. The inventors have additionally found that the aqueous phase separated from the caffeine-organic acid co-crystals can provide a decaffeinated coffee extract which is a useful source of chlorogenic acids.

STATEMENTS OF THE INVENTION

According to a first aspect of the invention there is provided a method for producing caffeine, wherein the method comprises:
(a) combining a coffee extract comprising caffeine with an aqueous organic acid;
(b) crystallizing the coffee extract and the aqueous organic acid so as to form caffeine-organic acid co-crystals in an aqueous phase;
(c) separating the caffeine-organic acid co-crystals from the aqueous phase; and
(d) extracting caffeine from the co-crystals obtained in step (c),
wherein step (d) comprises placing the co-crystals in an aqueous solution so as to form a caffeine precipitate and a solution comprising the organic acid.

The aqueous solution in step (d) may be an acidic solution or a basic solution. In one embodiment the solution is a basic solution with a pH of about 10 to about 14, e.g. a sodium hydroxide solution.

In one embodiment step (d) further comprises re-crystallizing caffeine and separating the caffeine crystals from the solution. In one embodiment the placing of the co-crystals in the solution is carried out at least 5 minutes before re-crystallizing caffeine, for example at least 5, 10, 15, 20, 30, 40, 50 or 60 minutes before re-crystallizing caffeine.

In one embodiment the method further comprises drying the aqueous phase obtained in step (c) so as to form a dried decaffeinated coffee extract. Drying of the aqueous phase may be by any method known in the art. Preferably the aqueous phase is dried by spray-drying, freeze-drying or vacuum drying.

Preferably the coffee extract comprises caffeine and chlorogenic acids and the dried decaffeinated coffee extract has a chlorogenic acids content which is higher than the chlorogenic acids content of the coffee extract used in step (a). The dried decaffeinated coffee extract has a caffeine content which is lower than the caffeine content of the coffee extract used in step (a).

In one embodiment the dried decaffeinated coffee extract has a chlorogenic acids content of from about 10 wt % to about 60 wt %, preferably from about 20 wt % to about 50 wt %, more preferably about 25 wt % to about 45 wt %. The weight percentage (wt %) of chlorogenic acids is determined with respect to the total weight of the dried decaffeinated coffee extract.

In one embodiment the method further comprises adding the caffeine extracted in step (d) to a food or beverage product.

In an alternative embodiment the method further comprises combining the caffeine extracted in step (d) with at least one of a pharmaceutically acceptable carrier, diluent or excipient to form a pharmaceutical composition.

According to a second aspect of the invention there is provided a method for producing a decaffeinated coffee extract comprising chlorogenic acids. The method comprises:
a. combining a coffee extract comprising caffeine and chlorogenic acids with an aqueous organic acid;
b. crystallizing the coffee extract and the aqueous organic acid so as to form caffeine-organic acid co-crystals in an aqueous phase;
c. separating the caffeine-organic acid co-crystals from the aqueous phase so as to form an aqueous decaffeinated coffee extract comprising chlorogenic acids; and drying the decaffeinated coffee extract comprising chlorogenic acids.

It is envisaged that the aqueous decaffeinated coffee extract comprising chlorogenic acids may be further processed in its application as a source of chlorogenic acids. For example the decaffeinated coffee extract comprising chlorogenic acids may be purified by any suitable purification method in the art to isolate the chlorogenic acids. The chlorogenic acids may further be subjected to a hydrolysis treatment to produce phenolic acids and/or quinic acid.

The coffee extract used in the first and second aspects of the invention may have a caffeine content of at least about 10 wt %. In one embodiment the coffee extract has a caffeine content of at least about 10, 15, 20, 25, 30, 35, 40, 45, 50, 55, 60, 65, 70, 75, 80, 85, 90 or 95 wt %, preferably a caffeine content of about 10 wt % to about 90 wt %, e.g. about 55 wt %. The weight percentage (wt %) of caffeine is determined with respect to the total weight of the coffee extract.

The coffee extract used in the first and second aspects of the invention is preferably a by-product or side-stream from a coffee decaffeination process. The terms "by-product" and "side-stream" as used herein are discussed in more detail below. The coffee decaffeination process from which the by-product or side-stream is generated may be any coffee decaffeination process known in the art. The only requirement is that the by-product or side-stream from the coffee decaffeination process includes caffeine.

In one embodiment the coffee extract is a by-product or side-stream from a coffee decaffeination process and has a caffeine content of at least about 10 wt %, preferably at least about 10 wt % to about 90 wt %, more preferably about 55 wt %.

In one embodiment the organic acid is selected from the group consisting of a hydroxybenzoic acid, a derivative of a hydroxybenzoic acid, a derivative of cinnamic acid and mixtures thereof. Preferably the organic acid is selected from the group consisting of a hydroxybenzoic acid, a derivative of a hydroxybenzoic acid, and mixtures thereof. More preferably the organic acid is a hydroxybenzoic acid or a derivative of a hydroxybenzoic acid.

In one embodiment the organic acid is selected from the group consisting of salicylic acid, gallic acid, vanillic acid, 3-hydroxybenzoic acid, 4-hydroxybenzoic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid, ellagic acid, caffeic acid, ferulic acid, p-coumaric acid and mixtures thereof.

In one embodiment the organic acid is selected from the group consisting of salicylic acid, gallic acid, vanillic acid, 3-hydroxybenzoic acid, 4-hydroxybenzoic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid, ellagic acid, ferulic acid, p-coumaric acid and mixtures thereof.

In another embodiment the organic acid is selected from salicylic acid, gallic acid, vanillic acid, 3-hydroxybenzoic acid, 4-hydroxybenzoic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid, and mixtures thereof, preferably 2,4-dihydroxybenzoic acid and/or 3,4-dihydroxybenzoic acid.

In one embodiment the method may further comprise adding the decaffeinated coffee extract comprising chlorogenic acids to a food or beverage product. The decaffeinated coffee extract may be added in its dried form or after re-suspension or dissolution of the extract in a liquid medium, e.g. an aqueous medium. The decaffeinated coffee extract may also be subjected to further processing before adding to a food or beverage product, e.g. to isolate the chlorogenic acids and/or to hydrolyse the chlorogenic acids to phenolic acids and/or quinic acids.

In another embodiment the method further comprises combining the decaffeinated coffee extract comprising chlorogenic acids with at least one of a pharmaceutically acceptable carrier, diluent or excipient to form a pharmaceutical composition. The decaffeinated coffee extract may be combined in its dried form or after re-suspension or dissolution in a liquid medium, e.g. an aqueous medium. The decaffeinated coffee extract may also be further processed before combining with at least one of a pharmaceutically acceptable carrier, diluent or excipient to form a pharmaceutical composition, e.g. to isolate the chlorogenic acids and/or to hydrolyse the chlorogenic acids to phenolic acids and/or quinic acids.

Unless indicated to the contrary, it will be understood by the skilled person that any description herein of features common to both the first and second aspects of the invention applies to both aspects.

DETAILED DESCRIPTION

The present invention is related to a method for producing caffeine and a method for producing a decaffeinated coffee extract comprising chlorogenic acids. Both methods involve combining a coffee extract with an aqueous organic acid.

Coffee Extract

As used herein the term "coffee extract" refers to a product obtained from an extraction process with coffee.

In one embodiment the coffee extract is the product obtained by extraction with coffee beans. For example the product obtained by contacting coffee beans with a solvent so as to dissolve soluble compounds in the solvent. Numerous methods for producing coffee extracts in this manner are known in the art. EP0916267 for example discloses the extraction of coffee from beans with water and/or steam. US20110223281 discloses the extraction of a green coffee extract from Coffee robusta beans by a hydroalcoholic extraction. The alcohol solvent used in US20110223281 is exclusively food quality alcohol.

The coffee beans used to prepare the coffee extract may be whole or ground. In one embodiment the coffee extract is prepared from ground green coffee beans. In another embodiment the coffee extract is prepared from green coffee beans which have been co-extracted with roasted coffee beans, i.e. green and roasted coffee beans may be extracted simultaneously in the same extraction system to yield a mixed extract.

The most volatile aroma components may be stripped from the coffee beans before extraction, e.g. if the caffeine produced by the method of the invention is to be used for the production of pure soluble coffee. Alternatively the most volatile aroma components may be stripped from the coffee extract. Methods for stripping of volatile aroma components are well known in the art, e.g. from EP1078576.

In an alternative embodiment the coffee extract is a commercially available product. For example the coffee extract may be a commercially available green coffee extract such as Svetol® brand green coffee extract, commercially available from NATUREX S.A., Avignon France. Svetol® Green Coffee Bean 400 mg includes caffeine and 45% chlorogenic acids.

The coffee extract may be a by-product or side-stream from a coffee decaffeination process.

As used herein the terms "by-product" or "side-stream" refer to a secondary or incidental product or output from a coffee decaffeination process. In other words a product/output which is not the major/primary product or output of the coffee decaffeination process: a product other than the decaffeinated product.

The by-product or side-stream may be from any coffee decaffeination process known in the art where free caffeine is present. For example the by-product or side-stream could be obtained from the water decaffeination technique as described in US2309092; from the use of a sugar-loaded activated carbon adsorbent as described in EP0008398; from the use of supercritical carbon dioxide as described in U.S. Pat. No. 4,260,639; from the use of solutions of esters of polyhydric alcohols and edible carboxylic acids as described in U.S. Pat. No. 3,682,648; from the use of water immiscible fatty materials as described in U.S. Pat. No. 4,465,699; or from the use of non-halogenated caffeine solvents other than fatty materials as described in U.S. Pat. No. 4,256,774.

As well as caffeine, a coffee extract may include other components such as chlorogenic acids, carbohydrates and fibre (e.g. sucrose, lignin, and pectin), protein and free amino acids, lipids (e.g. diterpenes), minerals and trigonelline. Preferably the coffee extract comprises caffeine and chlorogenic acids.

The coffee extract used in the methods of the invention preferably has a caffeine content of at least about 10 wt %. In one embodiment the coffee extract has a caffeine content of about 10, 15, 20, 25, 30, 35, 40, 45, 50, 55, 60, 65, 70, 75, 80, 85, 90 or 95 wt %. Preferably of about 10 wt % to about 90 wt %, more preferably about 15 wt % to about 85 wt %, still more preferably about 20 wt % to about 80 wt %, even more preferably about 25 wt % to about 75 wt % and most preferably about 30 wt % to about 70 wt %.

In one embodiment the coffee extract has a caffeine content of about 35 wt % to about 65 wt %, such as about 40 to about 60 wt %, e.g. about 55 wt %.

In one embodiment the coffee extract has a chlorogenic acids content of at least about 5 wt %; for instance, at least about 5, 10, 15, 20, 25, 30, 35, 40, 45 or 50 wt %. In one embodiment the coffee extract has a chlorogenic acids content of about 5 wt % to about 40 wt %, preferably about 10 wt % to about 35 wt %, more preferably about 15 wt % to about 30 wt %, and most preferably about 20 wt % to about 24 wt %, e.g. about 22 wt %.

Chlorogenic acids are a family of esters formed between trans-cinnamic acids and quinic acid. They are also referred to in the art as quinic acid diesters. Chlorogenic acids are naturally present in coffee, mainly as mono- and di-esters of quinic acid and phenolic groups (e.g. caffeic, ferulic, coumaric and methoxycinnamic) attached to different positions. In particular coffee naturally contains caffeoylquinic acids (such as e.g. 3-, 4-, or 5-caffeoylquinic acid), and diesters thereof, feruloyl quinic acids (such as e.g. 3-, 4-, or 5-feruloyl quinic acid) and diesters thereof.

In a further embodiment the coffee extract has a caffeine content of about 10 to about 90 wt % and a chlorogenic acids content of about 5 wt % to about 40 wt %. Preferably a caffeine content of about 15 wt % to about 85 wt % and a chlorogenic acids content of about 10 wt % to about 35 wt %. More preferably a caffeine content of about 20 wt % to about 80 wt % and a chlorogenic acids content of about 15 wt % to about 30 wt %. Most preferably a caffeine content of about 25 wt % to about 75 wt % and a chlorogenic acids content of about 20 wt % to about 24 wt %.

In a further embodiment the coffee extract has a caffeine content of about 10 to about 90 wt % and a chlorogenic acids content of about 10 wt % to about 35 wt %. Preferably a caffeine content of about 15 wt % to about 85 wt % and a chlorogenic acids content of about 15 wt % to about 30 wt %. More preferably a caffeine content of about 20 wt % to about 80 wt % and a chlorogenic acids content of about 20 wt % to about 24 wt %.

In a further embodiment the coffee extract has a caffeine content of about 15 wt % to about 85 wt % and a chlorogenic acids content of about 5 wt % to about 40 wt %. Preferably a caffeine content of about 20 wt % to about 80 wt % and a chlorogenic acids content of about 10 wt % to about 35 wt %. More preferably a caffeine content of about 25 wt % to about 75 wt % and a chlorogenic acids content of about 15 wt % to about 30 wt %.

Aqueous Organic Acid

As used herein, the phrase "aqueous organic acid" refers to an organic acid in an aqueous medium. The organic acid may for example be dissolved in water. Alternatively the organic acid may be suspended or dispersed in water.

When the organic acid is a solid at ambient temperature e.g. at 20° C., the solid organic acid may be combined with the coffee extract and subsequently dissolved or dispersed in water. Alternatively the organic acid is first prepared in the aqueous medium and than combined with the coffee extract.

As used herein, the term "combining" or the phrase "combined with" refers to the mixing of two substances, e.g. the mixing of a coffee extract with an organic acid. Any known method in the art can be used to combine or mix the two substances. When the organic acid is first prepared in the aqueous medium, either the coffee extract can be added to the aqueous organic acid or the aqueous organic acid can be added to the coffee extract. Alternatively both the coffee extract and the aqueous organic acid could be added to a mixing vessel simultaneously.

Preferably the organic acid should have a lower solubility in water at ambient temperature (20° C.) compared to caffeine. Preferably the organic acid has a water solubility of less than about 20 mg/ml at 20° C., more preferably less than about 15 mg/ml at 20° C., and most preferably less than about 10 mg/ml at 20° C.

In one embodiment the organic acid is selected from the group consisting of a hydroxybenzoic acid, a derivative of a hydroxybenzoic acid, a derivative of cinnamic acid or mixtures thereof. Preferably the organic acid is selected from the group consisting of a hydroxybenzoic acid, a derivative of a hydroxybenzoic acid or mixtures thereof. Most preferably the organic acid is a hydroxybenzoic acid or a derivative of a hydroxybenzoic acid.

As used herein the phrase "a hydroxybenzoic acid" refers to benzoic acids which have at least one hydroxy group, e.g. from one to five hydroxy groups. For example the hydroxybenzoic acid may be salicylic acid, 3-hydroxybenzoic acid, 4-hydroxybenzoic acid, 5-hydroxybenzoic acid, a dihydroxybenzoic acid (e.g. 2,3-dihydroxybenzoic acid, 2,4-dihydroxybenzoic acid, 3,4-dihydroxybenzoic acid etc.), a trihydroxybenzoic acid (e.g. gallic acid), a tetrahydroxybenzoic acid, a pentahydroxybenzoic acid, or mixtures thereof.

In one embodiment the hydroxybenzoic acid is selected from the group consisting of salicylic acid, 3-hydroxybenzoic acid, 4-hydroxybenzoic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid, gallic acid, and mixtures thereof.

As used herein the phrase "a derivative of a hydroxybenzoic acid" refers to a hydroxybenzoic acid as defined hereinabove which has been modified with at least one functional group. By the term "modified" is meant that the functional group replaces the hydrogen atom of at least one hydroxy group, or the functional group replaces at least one hydroxy group on the benzene ring of the benzoic acid, or the functional group is a substituent on the benzene ring of the benzoic acid. The latter is exemplified by the methyl group in orsellinic acid (2,4-dihydroxy-6-methylbenzoic acid).

The functional group may, for example, be an alkyl, alkenyl, alkynyl, amino, alkoxy, aryl, heterocyclyl, cycloalkyl, silyl, halo, acetyl, aminoalkyl, cyano, nitro, sulfanyl or phosphanyl group. Preferably the functional group is an alkyl, alkenyl, alkynyl, amino, alkoxy, silyl, acetyl, aminoalkyl, sulfanyl or phosphanyl group. More preferably the functional group is an alkyl, alkenyl, amino, alkoxy, acetyl or aminoalkyl group. It will be understood by the skilled person that the alkyl, alkenyl, alkynyl, amino, alkoxy, aryl, heterocyclyl, cycloalkyl, silyl, halo, acetyl, aminoalkyl, cyano, nitro, sulfanyl or phosphanyl group(s) used to modify the hydroxybenzoic acid may be optionally substituted.

In one embodiment the derivative of a hydroxybenzoic acid is a hydroxybenzoic acid which has at least one hydroxy group in which the hydrogen atom is replaced with a functional group. The functional group may be an alkyl, alkenyl, alkynyl, aryl, heterocyclyl or cycloalkyl group. Preferably the functional group is an alkyl, alkenyl or alkynyl group. More preferably the functional group is an alkyl group such as methyl, ethyl, propyl, butyl, pentyl, hexyl, isopropyl, isobutyl, sec-butyl, tert-butyl or neopentyl. Most preferred is methyl, ethyl, propyl, isopropyl, butyl, isobutyl, sec-butyl or neopentyl. Such derivatives are known in the art and include vanillic acid (4-hydroxy-3-methoxybenzoic acid), eudesmic acid (3,4,5-trimethoxybenzoic acid) and syringic acid (4-hydroxy-3,5-dimethoxybenzoic acid).

In one embodiment the derivative of a hydroxybenzoic acid is vanillic acid.

In one embodiment the organic acid is selected from the group consisting of a hydroxybenzoic acid, a derivative of a hydroxybenzoic acid, or mixtures thereof. For example, the organic acid may be selected from salicylic acid, 3-hydroxybenzoic acid, 4-hydroxybenzoic acid, 5-hydroxybenzoic acid, dihydroxybenzoic acids (e.g. 2,3-dihydroxybenzoic acid, 2,4-dihydroxybenzoic acid, 3,4-dihydroxybenzoic acid etc.), trihydroxybenzoic acids (e.g. gallic acid), tetrahydroxybenzoic acids, pentahydroxybenzoic acids, vanillic acid or mixtures thereof.

As used herein the phrase "derivative of cinnamic acid" refers to cinnamic acid which has been modified with functional groups on the benzene ring. Preferably the derivatives of cinnamic acid are hydroxycinnamic acids (hydroxycinnamates). For example the derivatives of cinnamic acid may include caffeic acid, ferulic acid, coumaric acid (o-, m- or p-coumaric acid) and mixtures thereof. In one embodiment the derivative of cinnamic acid is caffeic acid, ferulic acid or a mixture thereof. In another embodiment the derivative of cinnamic acid is p-coumaric acid.

Some of the organic acids used in the methods of the invention may exist as geometric isomers, e.g. they may possess one or more geometric centre and so may exist in two or more geometric forms. The present invention contemplates the use of all the individual geometric isomers of those organic acids, e.g. a derivative of trans-cinnamic acid.

In one embodiment the organic acid is selected from the group consisting of salicylic acid, gallic acid, 3-hydroxybenzoic acid, 4-hydroxybenzoic acid, vanillic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid, ellagic acid, vanillic acid, caffeic acid, ferulic acid, p-coumaric acid and mixtures thereof. Preferably the organic acid is selected from the group consisting of salicylic acid, gallic acid, vanillic acid, 3-hydroxybenzoic acid, 4-hydroxybenzoic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid and mixtures thereof. For example the organic acid may be 2,4-dihydroxybenzoic acid and/or 3,4-dihydroxybenzoic acid.

In one embodiment the organic acid is not caffeic acid.

The temperature at which the organic acid may be combined with the coffee extract will be readily determined by the skilled person. In one embodiment this temperature is maintained below the temperature at which the coffee extract degrades in flavour, e.g. below about 95° C. and above the freezing point of the aqueous system. Subsequent separation processes are preferably performed at, or above room temperature.

In another embodiment the temperature at which the organic acid is combined with the coffee extract is maintained below the temperature at which the chlorogenic acids in the coffee extract degrade, e.g. below about 85° C. For example, the temperature for step (a) may be in the range of about 0° C. to about 85° C., preferably in the range of 20° C. to about 80° C.

The temperature at which the organic acid is combined with the coffee extract may be important for the second aspect of the invention because it avoids any significant degradation of the chlorogenic acids present in the coffee extract.

In one embodiment the mole ratio of caffeine (in the coffee extract) to organic acid is at least about 0.5:1, for example from about 0.5:1 to about 3:1. In one embodiment the mole ratio of caffeine in the coffee extract to organic acid is from about 0.75:1 to about 2.75:1 or from about 1:1 to about 2.5:1. Preferably the mole ratio of caffeine to organic acid matches the stoichiometry of the co-crystal formed so as to ensure that substantially all of the organic acid complexes with the caffeine. For example caffeine and vanillic acid form a co-crystal at a ratio of 2:1 whereas caffeine and 2,4-dihydroxybenzoic acid form a co-crystal at a ratio of 1.1.

Crystallisation

According to the present invention the coffee extract is crystallized with the aqueous organic acid so as to form caffeine-organic acid co-crystals in an aqueous phase. As used herein, the term "co-crystal" refers to a solid that is a crystalline single phase material composed of two or more different compounds in a stoichiometric ratio which are neither solvates nor simple salts. The co-crystal according to the present invention may be in a hydrated form, for example comprising one or two water molecules in stoichiometric ratio with other compounds in the crystal structure.

In one embodiment the co-crystals are formed by leaving the combination of coffee extract comprising caffeine and aqueous organic acid to stand for a period of time, e.g. for at least one hour or at least two hours. The growth of the crystals may be aided by maintaining the temperature of the coffee extract between about 0° C. and 50° C.

Crystal growth may also be made more rapid by seeding, i.e. by incorporating caffeine-organic acid co-crystals that have already formed into the mixture. The appropriate level of seeding will depend on the coffee extract and will be readily determined by the person skilled in the art using routine methods.

In another embodiment the co-crystals are formed by cycling the temperature of the combination between about 85° C. and about 0° C., preferably between about 80° C. and about 0° C. It is believed that cycling the temperature in this manner promotes the formation of larger co-crystals which are easier to separate from the aqueous phase, e.g. by filtration.

Separation

The caffeine-organic acid co-crystals are separated from the aqueous phase in the first and second aspects of the invention. Any method known in the art for separating a liquid phase and a solid phase may be used. In one embodiment the separation of the caffeine-organic acid co-crystals from the aqueous phase is carried out by filtration or centrifugation. The co-crystals may also be washed with distilled water after separation.

Extraction

According to the present invention, caffeine is extracted from the co-crystals formed in step (c). The caffeine extraction comprises placing the co-crystals in an aqueous solution so as to form a caffeine precipitate and a solution comprising the organic acid.

In one embodiment the aqueous solution used for extraction is an acidic solution with a pH of about 2 to about 5, preferably about 2 to about 4.

In another embodiment the aqueous solution used for extraction is a basic solution with a pH of about 10 to about 14, preferably with a pH of about 11 to about 13.

Preferably the aqueous solution used for extraction is a basic solution with a pH of about 10 to about 14. For example, the basic solution may be selected from a sodium hydroxide solution, a potassium hydroxide solution and a calcium hydroxide solution. In one embodiment the basic solution is a sodium hydroxide solution.

The co-crystals may be placed in the aqueous solution under agitation (e.g. stirring) so as to separate the co-crystals and form a caffeine precipitate and a solution comprising the organic acid. Preferably the organic acid is dissolved in the solution in the form of a salt.

In one embodiment the co-crystals may be placed in the aqueous solution at a concentration of about 50 to about 500 g/L, preferably about 100 to about 450 g/L, more preferably about 150 g/L to about 400 g/L, most preferably about 200 g/L to about 350 g/L.

Once formed, the caffeine precipitate may be separated from the solution comprising the organic acid. Any separation method known in the art may be used, e.g. filtration or centrifugation.

The extracted caffeine (caffeine precipitate) may be re-crystallized. Any crystallisation method known in the art may be used to form the re-crystallized caffeine, e.g. by increasing the concentration of the co-crystals in the solution. Any separation method known in the art may be used to subsequently separate the caffeine from the solution, e.g. filtration or centrifugation.

In one embodiment placing of the co-crystals in the solution is carried out at least about 5 minutes before re-crystallizing caffeine, for example about 5 minutes to about 60 minutes before, preferably about 5 minutes to about 20 minutes before. It is believed that at least 5 minutes allows at least part of the co-crystals to be dissolved and separated by the aqueous solution. Crystallization of caffeine may occur without all the co-crystals having dissolved. In effect there is a change in the nature of the solid phase from the co-crystal to caffeine.

Food or Beverage Product

In one embodiment the method further comprises adding the caffeine extracted in step (d) to a food or beverage product.

In another embodiment the method further comprises adding the decaffeinated coffee extract comprising chlorogenic acids to a food or beverage product.

The decaffeinated coffee extract comprising chlorogenic acids may be subjected to further processing before it is added to a food or beverage product. For example, the decaffeinated coffee extract may be subjected to a purification treatment or the like to isolate or separate the chlorogenic acids and the chlorogenic acids subsequently added to a food or beverage product. The chlorogenic acids may also be subjected to a hydrolysis treatment before, during or after being added to a food or beverage product, e.g. to produce phenolic acids and/or quinic acid.

Any purification or hydrolysis treatment known in the art may be used.

By the term "adding" used herein is meant the use of the caffeine, decaffeinated coffee extract, chlorogenic acids, phenolic acids and/or quinic acid as an ingredient of said food or beverage product.

When used as an ingredient of a food or beverage product, the caffeine, decaffeinated coffee extract, chlorogenic acids, phenolic acids and/or quinic acid may be added at any appropriate step in the production process of said food or beverage product to achieve the desired effect. The caffeine, decaffeinated coffee extract, chlorogenic acids, phenolic acids and/or quinic acid may also be added in any amount suitable to bring about the desired effect.

The food or beverage product may be any food or beverage product known in the art. For example, the food or beverage product may be a coffee product, a tea beverage, a soft drink, water (e.g. bottled water), a dietary supplement, a nutritional supplement, a dairy product (e.g. yoghurt, milk powder, milk-based dessert), a cereal product, a fruit or vegetable juice product, or a confectionary product. Preferably the food or beverage product is a beverage product such as coffee, tea, a soft drink, a fruit or vegetable juice product or water (e.g. bottled water).

In one embodiment the caffeine produced by the method of the first aspect of the invention is added to a coffee product, e.g. a soluble coffee product or a ready-to-drink coffee product. A soluble coffee product may be produced by mixing the extracted caffeine with a coffee extract which has not been combined with an aqueous organic acid according to the method of the invention. Methods for producing a soluble coffee product from coffee extracts are well known in the art.

The compositions, or food or beverage products of the present invention may contain (e.g. may have been supplemented with) additional vitamins, minerals and micronutrients, including trace elements, in accordance with the recommendations (e.g. recommended daily intake guidelines) of government bodies.

Pharmaceutical Composition

In one embodiment the first aspect of the invention comprises combining the caffeine extracted in step (d) with at least one of a pharmaceutically acceptable carrier, diluent or excipient to form a pharmaceutical composition.

In another embodiment the second aspect of the invention comprises combining the decaffeinated coffee extract comprising chlorogenic acids with at least one of a pharmaceutically acceptable carrier, diluent or excipient to form a pharmaceutical composition.

The decaffeinated coffee extract may be combined in its dried form or after re-suspension or dilution in a pharmaceutically acceptable medium.

The decaffeinated coffee extract may also be combined with at least one of a pharmaceutically acceptable carrier, diluent or excipient after further processing. For example, the decaffeinated coffee extract may be subjected to a purification treatment or the like to isolate or separate the chlorogenic acids and the chlorogenic acids subsequently combined with at least one of a pharmaceutically acceptable carrier, diluent or excipient to form a pharmaceutical composition. The chlorogenic acids may also be subjected to a hydrolysis treatment before, during or after being combined with at least one of a pharmaceutically acceptable carrier, diluent or excipient to form a pharmaceutical composition, e.g. to produce phenolic acids and/or quinic acid. Any purification or hydrolysis treatment known in the art may be used.

Examples of such suitable excipients for compositions described herein may be found in the "Handbook of Pharmaceutical Excipients, 2nd Edition, (1994), Edited by A Wade and P J Weller. Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like.

Examples of suitable diluents include ethanol, glycerol and water.

The choice of pharmaceutical carrier, excipient or diluent can be selected with regard to the intended route of administration and standard pharmaceutical practice.

The pharmaceutical compositions may comprise as, or in addition to, the carrier, excipient and/or diluent any suitable binder(s), lubricant(s), suspending agent(s), coating agent(s) and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used. Nutritionally acceptable carriers, diluents and excipients include those suitable for human or animal consumption and that are used as standard in the food industry. Typical nutritionally acceptable carriers, diluents and excipients will be familiar to the skilled person in the art.

Uses of the Extracted Caffeine

The caffeine produced by the method of the first aspect of the invention is of substantially high purity. This is advantageous because it allows the extract to be used in various applications without further purification and/or refinement. Uses of caffeine are far-reaching and include the pharmaceutical, nutritional and cosmetic sectors. One particular advantage of the caffeine extract obtained by the method of the present invention is that it is food-grade.

Uses of the Decaffeinated Coffee Extract Comprising Chlorogenic Acids

The decaffeinated coffee extract produced by the second aspect of the invention is also advantageous because it can be used as a source of chlorogenic acids and chlorogenic acids are known in the art to provide health benefits. US20110223281 for instance discloses that a decaffeinated green coffee extract containing 6% to 8% of 4-caffeoylquinic acid and having a total chlorogenic acid concentration that exceeds about 45% is useful for controlling body weight in humans.

Chlorogenic acids are also hydrolysed to form phenolic acids such as ferulic acid and caffeic acid, and the antioxidant activity of the phenolic acids produced from coffee-originating chlorogenic acids is known to protect against "oxidative stress" by reducing damaging free radicals that may be implicated, e.g. in cancer, heart disease, degenerative brain disorders and ageing. EP1090635 A2 discloses a method for treating hypertension, a cardiac disease or a cerebrovascular disease comprising administration of ferulic acid or salt thereof to a subject in need thereof. Hydrolysis of chlorogenic acids also produces quinic acid which is believed to have health benefit, e.g. due to its in-situ effect on antioxidants in the human body (Pero et al., International Journal of Biotechnology and Biochemistry (2009) 5, 293-305).

The decaffeinated coffee extract comprising chlorogenic acids is therefore advantageous because as a source of chlorogenic acids it can be used to produce phenolic acids and/or quinic acid.

It should be noted that embodiments and features described in the context of one of the aspects of the present invention also apply to the other aspects of the invention.

All patent and non-patent references cited in the present application are hereby incorporated by reference in their entirety.

EXAMPLES

The invention will now be described in further detail in the following non-limiting examples.

The practice of the present invention will employ, unless otherwise indicated, conventional techniques of chemistry which are within the capabilities of a person of ordinary skill in the art. Such techniques are explained in the literature.

Example 1

Co-Crystal Formation With Different Organic Acids

Co-crystals were formed according to the method of the invention. The experimental details for each co-crystal formation are set out in Tables 1a and b below.

TABLE 1a

| Experiment No. | 1 | 2 | 3 | 4 | 5 | 6 | 7 |
|---|---|---|---|---|---|---|---|
| Organic acid | Caffeic acid | Ferulic acid | Gallic acid | Salicylic acid | 3-hydroxybenzoic acid | 4-hydroxybenzoic acid | Ellagic acid |
| Coffee extract comprising caffeine (g) | 10 | 10 | 10 | 10 | 10 | 10 | 3.5 |
| Organic acid (g) | 5.1 | 5.5 | 4.8 | 3.9 | 3.9 | 3.9 | 3 |
| Water (g) | 60 | 50 | 80 | 55 | 60 | 50 | 20 |

TABLE 1b

| Experiment No. | 8 | 9 | 10 | 11 | 12 |
|---|---|---|---|---|---|
| Organic acid | Vanillic acid | 2,3-dihydroxybenzoic acid | 2,4-dihydroxybenzoic acid | 2,5-dihydroxybenzoic acid | 3,4-dihydroxybenzoic acid |
| Coffee extract comprising caffeine (g) | 10 | 10 | 10 | 10 | 10 |
| Organic acid (g) | 4.8 | 4.4 | 4.4 | 4.4 | 4.4 |
| Water (g) | 40 | 50 | 30 | 50 | 50 |

A coffee extract comprising caffeine was dissolved in water and, after complete dissolution the organic acid was added. The coffee extract was dissolved at a temperature between 20° C. and 80° C., typically 25° C. The initial coffee extract used in each experiment was a green coffee extract with a caffeine content of about 55 wt % and a chlorogenic acids content of about 22 wt %. The molar ratio of caffeine: organic acid in each experiment was about 1:1.

Co-crystals formed spontaneously with all the organic acids used. After separating the caffeine-organic acid co-crystals from the aqueous phase by filtration, several of the co-crystals were analysed by X-ray powder diffraction. The XRPD patterns for the co-crystals obtained with salicylic acid, ellagic acid and 4-hydroxybenzoic acid can be seen in FIGS. 1 to 3 where the top pattern is the calculated pattern for each respective co-crystal using Mercury software from the Cambridge Structural Database, and the bottom pattern is the measured pattern for the co-crystals formed in Example 1.

Figure 1:
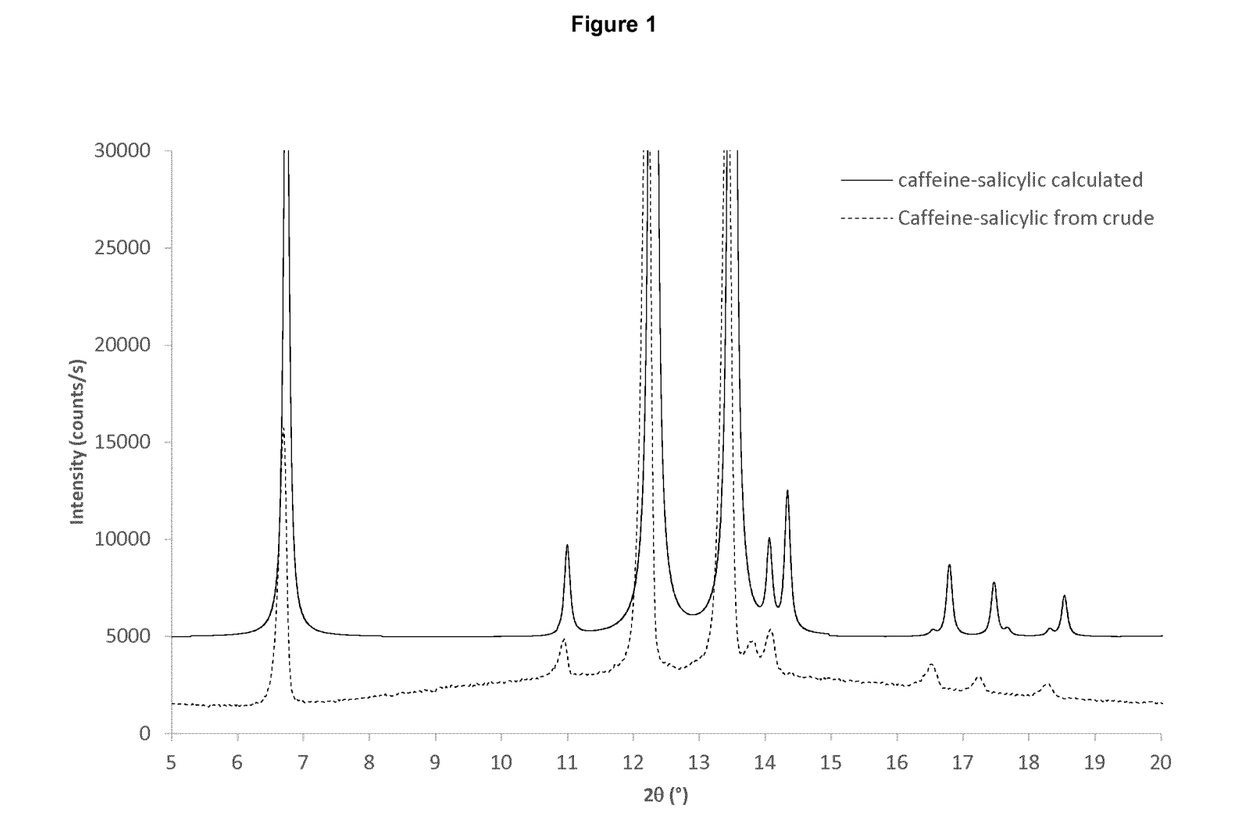
FIG. 1 contains X-ray powder diffraction patterns for caffeine-salicylic acid co-crystals. The upper or top XRPD pattern is calculated for a caffeine-salicylic acid co-crystal based on information from the literature (Cambridge Structural Database). The bottom or lower XRPD pattern is for the caffeine-salicylic acid co-crystal prepared in Example 1.
Figure 2:
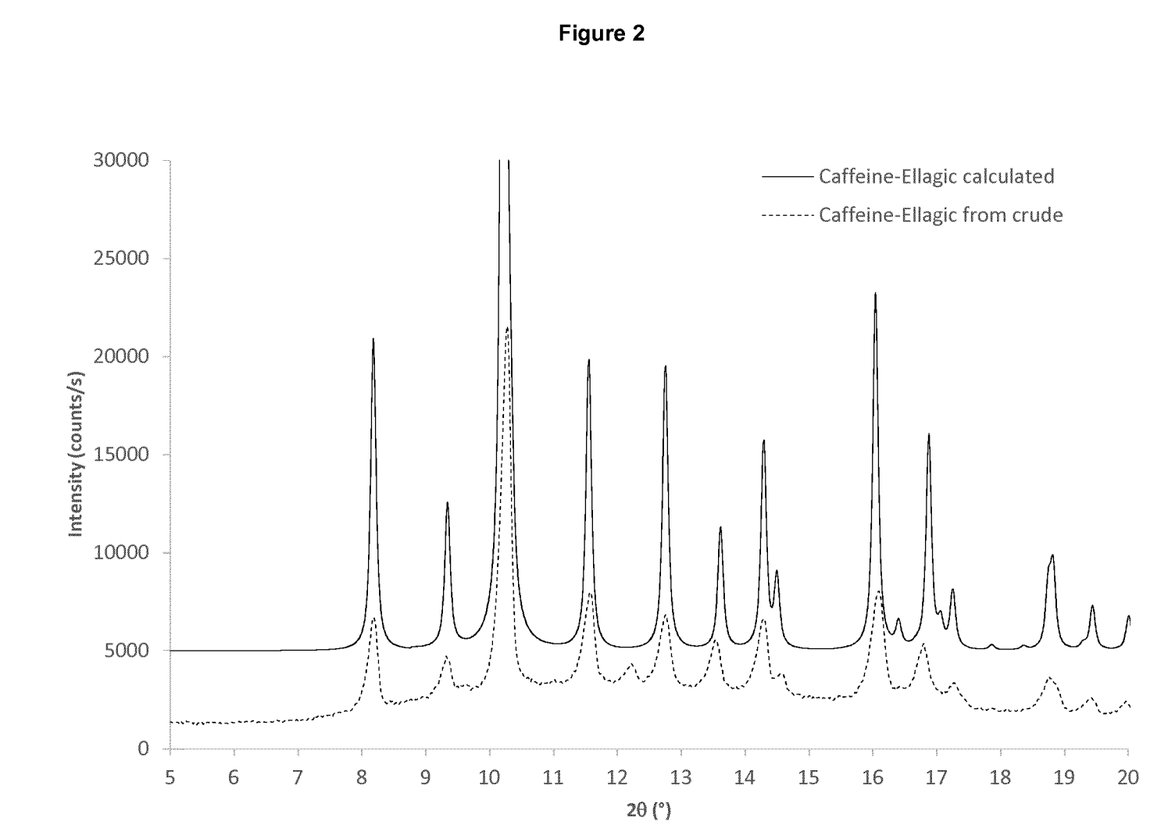
FIG. 2 contains X-ray powder diffraction patterns for caffeine-ellagic acid co-crystals. The upper or top XRPD pattern is calculated for a caffeine-ellagic acid co-crystal based on information from the literature (Cambridge Structural Database). The bottom or lower XRPD pattern is for the caffeine-ellagic acid co-crystal prepared in Example 1.
Figure 3:
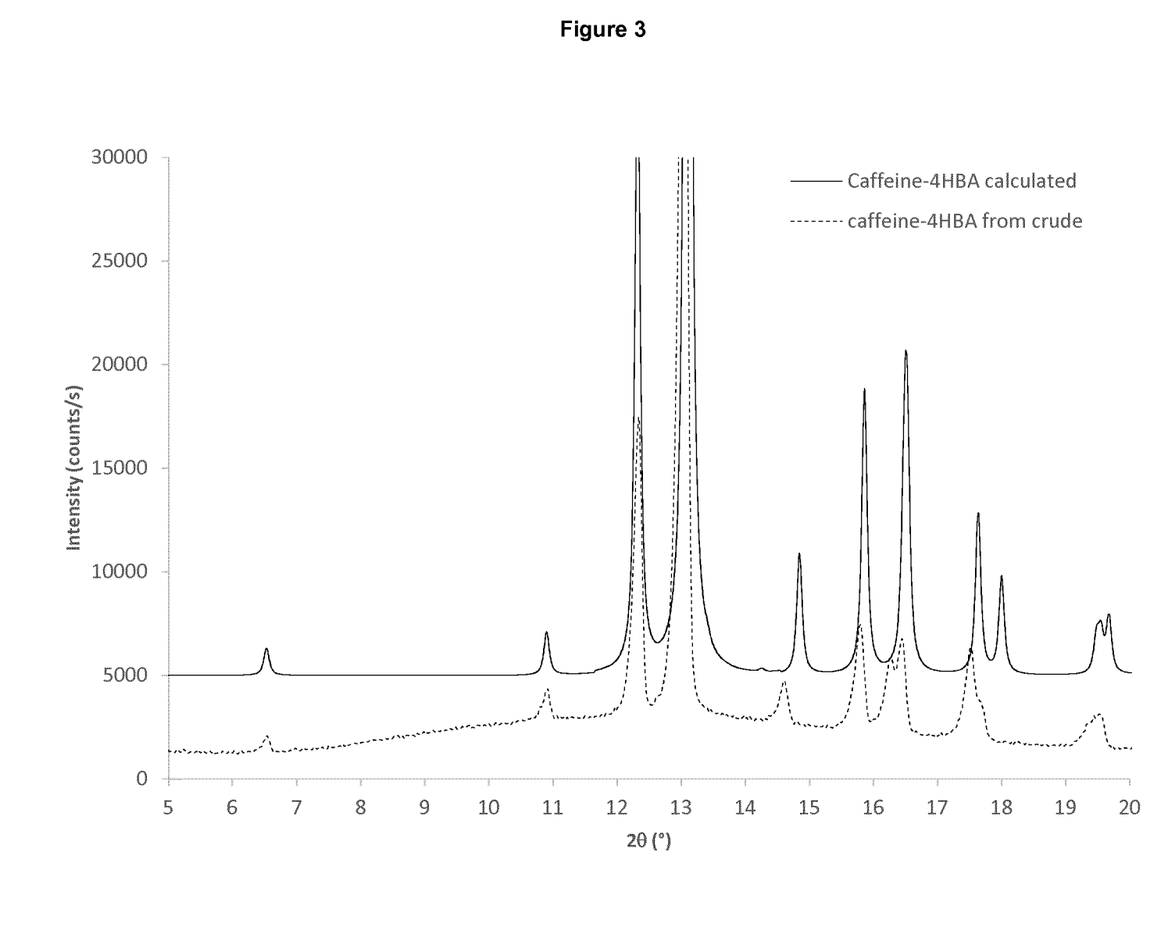
FIG. 3 contains X-ray powder diffraction patterns for caffeine-4-hydroxybenzoic acid co-crystals. The upper or top XRPD pattern is calculated for a caffeine-4-hydroxybenzoic acid co-crystal based on information from the literature (Cambridge Structural Database). The bottom or lower XRPD pattern is for the caffeine-4-hydroxybenzoic acid co-crystal prepared in Example 1.

It can be seen from FIGS. 1 to 3 that the co-crystals formed in Example 1 were comparable to the calculated XRPD patterns for each organic acid.

Example 2

Analysis of the Aqueous Phase Separated From Each of the Co-Crystals

The aqueous phase separated from the co-crystals in each experiment of Table 1 was also analysed by high-performance liquid chromatography (HPLC) using known methods. The composition of these aqueous phases is set out below in Tables 2a and 2b below.

TABLE 2a

| Experiment No. | 1 | 2 | 3 | 4 | 5 | 6 | 7 |
|---|---|---|---|---|---|---|---|
| Organic acid | Caffeic acid | Ferulic acid | Gallic acid | Salicylic acid | 3-hydroxybenzoic acid | 4-hydroxybenzoic acid | Ellagic acid |
| Chlorogenic acids (wt %) | 45 | 34 | 32 | 31 | 30 | 25 | 40 |

TABLE 2b

| Experiment No. | 8 | 9 | 10 | 11 | 12 |
|---|---|---|---|---|---|
| Organic acid | Vanillic acid | 2,3-dihydroxybenzoic acid | 2,4-dihydroxybenzoic acid | 2,5-dihydroxybenzoic acid | 3,4-dihydroxybenzoic acid |
| Caffeine (wt %) | 20 | 19 | 3 | 17 | 9 |
| Chlorogenic acids (wt %) | 34 | 38 | 42 | 33 | 38 |

It can be seen from the results in Tables 2a and 2b that in one aspect the present invention provides a decaffeinated coffee extract with a relatively high content of chlorogenic acids. In particular the results show how from a coffee extract with a chlorogenic acids content of about 22 wt %, the present invention provides a decaffeinated coffee extract with a chlorogenic acids content of from 25 to 45 wt %.

The decaffeinated coffee extract provided by the present invention is therefore a useful source of chlorogenic acids. This is advantageous because chlorogenic acids are known to provide health benefits either when used directly or after they have been hydrolysed into phenolic acids and/or quinic acid.

Example 3

Figure 4:
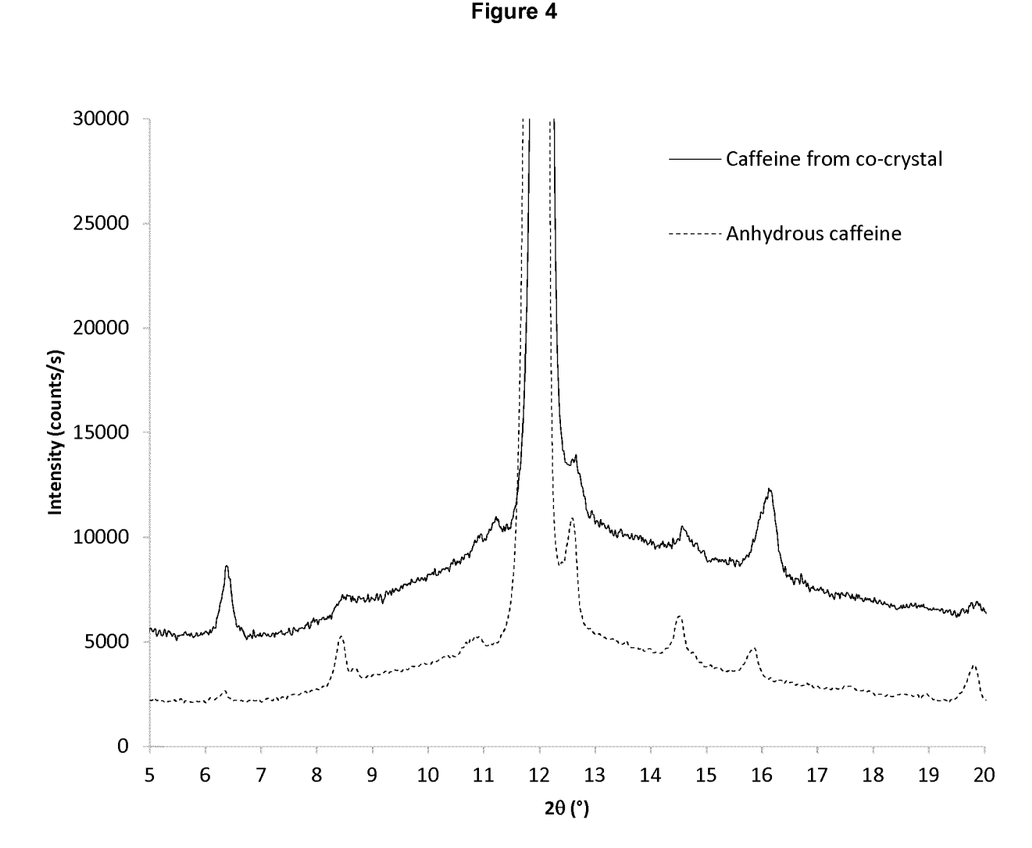
FIG. 4 contains X-ray powder diffraction patterns for caffeine. The upper or top XRPD pattern is for the caffeine produced in Example 3 according to the method of the present invention. The bottom or lower XRPD pattern is for commercially available anhydrous caffeine (Sigma-Aldrich).

Extraction of Caffeine From a Caffeine-Salicylic Acid Co-Crystal 2.4 g of the co-crystal formed in Example 1 between caffeine and salicylic acid was placed in 10 ml of a 6M sodium hydroxide solution. After 15 minutes under stirring, the separation of both the liquid and solid phases allowed pure caffeine to be harvested with a yield of 83%. The liquid and solid phases were separated by filtration. The XRPD analysis of the separated caffeine confirmed the formation of anhydrous caffeine. This can be seen from the XRPD pattern in FIG. 4 where the top pattern is for the caffeine obtained in Example 3 and the bottom pattern is for commercial anhydrous caffeine (Sigma-Aldrich).

The invention claimed is:

1. A method for producing caffeine, wherein the method comprises:
    a. combining a coffee extract comprising caffeine with an aqueous organic acid;
    b. crystallizing the coffee extract and the aqueous organic acid so as to form caffeine-organic acid co-crystals in an aqueous phase;
    c. separating the caffeine-organic acid co-crystals from the aqueous phase; and
    d. extracting caffeine from the co-crystals obtained in step (c);
    wherein step (d) comprises placing the co-crystals in an aqueous solution so as to form a caffeine precipitate and a solution comprising the organic acid.

2. The method according to claim 1, wherein the solution in step (d) is a basic solution with a pH of about 10 to about 14.

3. The method according to claim 1, wherein step (d) further comprises re-crystallizing caffeine and separating the caffeine crystals from the solution.

4. The method according to claim 3, wherein the placing of the co-crystals in the solution is carried out at least 5 minutes before re-crystallizing caffeine.

5. The method according to claim 1, wherein the method further comprises drying the aqueous phase separated from the co-crystals in step (c) so as to form a dried decaffeinated coffee extract.

6. The method according to claim 1, wherein the method further comprises adding the caffeine extracted in step (d) to a food or beverage product.

7. The method according to claim 1 wherein the method further comprises combining the caffeine extracted in step (d) with at least one of a pharmaceutically acceptable carrier, diluent or excipient to form a pharmaceutical composition.

8. A method for producing a decaffeinated coffee extract comprising chlorogenic acids, wherein the method comprises:
    a. combining a coffee extract comprising caffeine and chlorogenic acids with an aqueous organic acid;
    b. crystallizing the coffee extract and the aqueous organic acid so as to form caffeine-organic acid co-crystals in an aqueous phase; and
    c. separating the caffeine-organic acid co-crystals from the aqueous phase so as to form an aqueous decaffeinated coffee extract comprising chlorogenic acids; and drying the decaffeinated coffee extract comprising chlorogenic acids.

9. The method according to claim 8, wherein the coffee extract has a caffeine content of at least about 10 wt %.

10. The method according to claim 8, wherein the coffee extract has a caffeine content of about 10 wt % to about 90 wt %.

11. The method according to claim 8, wherein the coffee extract is a by-product or side-stream from a coffee decaffeination process.

12. The method according to claim 8 wherein the organic acid is selected from the group consisting of a hydroxybenzoic acid, a derivative of a hydroxybenzoic acid, a derivative of cinnamic acid and mixtures thereof.

13. The method according to claim 8, wherein the organic acid is a hydroxybenzoic acid.

14. The method according to claim 1, wherein the organic acid is selected from the group consisting of salicylic acid, gallic acid, vanillic acid, 3-hydroxybenzoic acid, 4-hydroxybenzoic acid, 2,3-dihydroxybenzoic acid, 3,5-dihydroxybenzoic acid, 2,4-dihydroxyb enzoic acid, 2,5-dihydroxybenzoic acid, 3,4-dihydroxybenzoic acid, ellagic acid, caffeic acid, ferulic acid, p-coumaric acid and mixtures thereof.

15. The method according to claim 14, wherein the organic acid is selected from the group consisting of salicylic acid, gallic acid, vanillic acid, 3-hydroxybenzoic acid, 4-hydroxybenzoic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid and mixtures thereof.

16. The method according to claim 1, wherein the organic acid is a hydroxybenzoic acid.

17. The method according to claim 16, wherein the organic acid is selected from the group consisting of salicylic acid, gallic acid, vanillic acid, 3-hydroxybenzoic acid, 4-hydroxybenzoic acid, 2,3-dihydroxybenzoic acid, 3,5-dihydroxybenzoic acid, 2,4-dihydroxybenzoic acid, 2,5-dihydroxybenzoic acid, 3,4-dihydroxybenzoic acid, ellagic acid, caffeic acid, ferulic acid, p-coumaric acid and mixtures thereof.

\* \* \* \* \*

UNITED STATES PATENT AND TRADEMARK OFFICE
CERTIFICATE OF CORRECTION

Page 1 of 1

PATENT NO. : 11,252,975 B2
APPLICATION NO. : 16/650022
DATED : February 22, 2022
INVENTOR(S) : Julien Philippe Nicolas Mahieux et al.

It is certified that error appears in the above-identified patent and that said Letters Patent is hereby corrected as shown below:

On the Title Page

Item (72),
The inventor's name should be changed from "QERTIING, Heiko" to "OERTLING, Heiko."
The inventor's name should be changed from "ROQUET, Laure" to "POQUET, Laure."

Signed and Sealed this
Twenty-sixth Day of April, 2022

Katherine Kelly Vidal
*Director of the United States Patent and Trademark Office*